United States Patent
Boutet et al.

(10) Patent No.: US 10,073,022 B2
(45) Date of Patent: Sep. 11, 2018

(54) METHOD FOR DETERMINING A CONCENTRATION OF LIPIDS IN A MICROORGANISM

(71) Applicant: COMMISSARIAT A L'ENERGIE ATOMIQUE ET AUX ENERGIES ALTERNATIVES, Paris (FR)

(72) Inventors: Jerome Boutet, Claix (FR); Cedric Allier, Grenoble (FR); Giovanni Finazzi, Paris (FR); Eric Marechal, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 4 days.

(21) Appl. No.: 15/121,214

(22) PCT Filed: Feb. 23, 2015

(86) PCT No.: PCT/EP2015/053676
§ 371 (c)(1),
(2) Date: Aug. 24, 2016

(87) PCT Pub. No.: WO2015/128271
PCT Pub. Date: Sep. 3, 2015

(65) Prior Publication Data
US 2017/0010200 A1    Jan. 12, 2017

(30) Foreign Application Priority Data
Feb. 25, 2014 (FR) .................. 14 51495

(51) Int. Cl.
*G06K 9/00* (2006.01)
*G01N 15/06* (2006.01)
(Continued)

(52) U.S. Cl.
CPC ............ *G01N 15/06* (2013.01); *C12M 41/38* (2013.01); *G01N 15/0211* (2013.01);
(Continued)

(58) Field of Classification Search
None
See application file for complete search history.

(56) References Cited

U.S. PATENT DOCUMENTS 6,028,663 A * 2/2000 O'Mongain ........... G01N 21/31
356/213
7,132,254 B2 * 11/2006 Vincent .................. G01N 21/31
356/213
(Continued)

OTHER PUBLICATIONS

Allier et al., "Lensfree microscopy: a new framework for the imaging of viruses, bacteria, cells and tissue", 2015 IEEE International Electron Devices Meeting (IEDM), Dec. 7-9, 2015, pp. 13.4.1-13.4.5.*
(Continued)

*Primary Examiner* — Matthew Bella
*Assistant Examiner* — Jose M Torres
(74) *Attorney, Agent, or Firm* — Oblon, McClelland, Maier & Neustadt, L.L.P.

(57) ABSTRACT

A method and a device for determining a concentration of lipids in a microorganism such as a micro-alga by illuminating a sample containing microorganisms and acquiring a total diffraction pattern of the sample is acquired, the total diffraction pattern including a plurality of unit diffraction pattern each associated with a microorganism.

10 Claims, 3 Drawing Sheets (51) Int. Cl.
G01N 21/47 (2006.01)
G01N 33/483 (2006.01)
G01N 15/02 (2006.01)
C12M 1/34 (2006.01)

(52) U.S. Cl.
CPC ..... *G01N 21/4788* (2013.01); *G01N 33/4833* (2013.01); *G01N 2015/0693* (2013.01)

(56) References Cited

U.S. PATENT DOCUMENTS

| | | | | |
|---|---|---|---|---|
| 8,244,477 | B1* | 8/2012 | Embaye | G01N 33/0098 702/19 |
| 2010/0273209 | A1* | 10/2010 | Eden | B01L 3/5082 435/39 |
| 2014/0248713 | A1* | 9/2014 | Allier | G02B 27/42 436/501 |
| 2014/0287449 | A1* | 9/2014 | Bonyuet | C12Q 1/02 435/29 |
| 2015/0087014 | A1* | 3/2015 | Weissman | C12Q 1/04 435/34 |

OTHER PUBLICATIONS

Allier et al., "Video lensfree microscopy of 2D and 3D culture of cells", Proc. SPIE 8947, Imaging, Manipulation, and Analysis of Biomolecules, Cells, and Tissues XII, 89471 H, Mar. 4, 2014, pp. 89471H-1-89471H-9.*

French Preliminary Search Report dated Aug. 7, 2014 in FR 1451495 (with English translation of categories of cited documents).

International Search Report dated May 20, 2015 in PCT/EP2015/053676.

Dan Fu, et al., "Quantitative Chemical Imaging with Multiplex Stimulated Raman Scattering Microscopy" Journal of the American Chemical Society, vol. 134, XP055133192, 2012, pp. 3623-3626.

Alon Greenbaum, et al., "Imaging without lenses: achievements and remaining challenges of wide-field on-chip microscopy" Nature Methods, vol. 9, No. 9, XP002698190, Sep. 2012, pp. 889-895.

C.P. Allier, et al., "Bacteria detection with thin wetting film lensless imaging" Biomedical Optics Express, vol. 1, No. 3, XP0550665387, Oct. 1, 2010, pp. 762-770.

Monika E. Dolega, et al., "Label-free analysis of prostate acini-like 3D structures by lensfree imaging" Biosensors and Bioelectronics, vol. 49, XP055132939, 2013, pp. 176-183.

J.-P.Cadoret, et al. "La production de biocarburant lipidique avec des microalgues: promesses et défis" Journal de la Société de Biologie, vol. 202, No. 3, XP055133243, 2008, pp. 201-211.

Paul J. Harrison, et al., "A broad spectrum artificial seawater medium for coastal and open ocean phytoplankton" Journal of Phycology, vol. 16, 1980, pp. 28-35.

John A. Berges, et al., "Evolution of an artificial seawater medium: improvements in enriched seawater, artificial water over the last two decades" Journal of Phycology, vol. 37, 2001, pp. 1138-1145.

* cited by examiner

FIG 6 under parallel in the image of a page from US 10,073,022 B2.

METHOD FOR DETERMINING A CONCENTRATION OF LIPIDS IN A MICROORGANISM

TECHNICAL FIELD

The present invention relates to the field of methods for determining a concentration of lipids in a microorganism, in particular micro-algae.

The invention also relates to a device for implementing such a method.

STATE OF PRIOR ART

A micro-algae is a microscopic organism, for example of the unicellular type, and the size of which typically ranges from a few micrometers to a few hundreds micrometers. Micro-algae typically contain photosynthetic organisms living essentially in water. The micro-algae have an interest in particular in the field of biofuels, because of their lipid storage properties, these lipids being then apt be used for producing fuels.

In comparison with the traditional biofuel sources, micro-algae have many advantages, from which a very quick biomass growth, a low water consumption, the lack of need for an arable land because they are cultivated in open-air pools or in bioreactors. They also provide an advantageous means of reusing $CO_2$ produced by some industries. The number of species of micro-algae is assessed to 200 000, of which only 35 000 have been studied to date. Therefore, it is highly probable that species of micro-algae particularly efficient within the scope of biomass production are discovered soon, to which can be added the possibility of creating new alternatives by genetic engineering techniques.

The culture of micro-algae within the scope of biomass production implements a lipid storage phase by micro-algae, for obtaining lipid-rich micro-algae. This step requires the evolution of the concentration of lipids in micro-algae to be known.

In prior art, a method for measuring the concentration of lipids in micro-algae is known, consisting in taking a sample of micro-algae which is contacted with a fluorescent label called Nile red. The fluorescent label is all the more attached to the micro-algae that they are rich in lipids, such that a fluorescence signal with an intensity proportional to the concentration of lipids in the micro-algae is detected. One drawback of this method is that it is destructive for the sample, because the fluorescent label is toxic for micro-algae. Therefore, it cannot be implemented in situ, in a bioreactor or a pool receiving a culture of micro-algae.

One purpose of the present invention is to provide a non destructive method for measuring a concentration of lipids in microorganisms such as micro-algae.

Another object of the present invention is to provide a device for implementing such a method.

DISCLOSURE OF THE INVENTION

This purpose is achieved with a method for determining a concentration of lipids in a microorganism, in particular micro-algae, in which:
  a sample containing microorganisms is illuminated; and
  a total diffraction pattern of the sample is acquired, the total diffraction pattern comprising a plurality of unit diffraction patterns each associated with a microorganism.

The method according to the invention further comprises the following steps:
  determining a value of a numerical indicator representative of a dispersion of the light intensity in a zone of interest of the total diffraction pattern, said zone of interest comprising at least one unit diffraction pattern, and each unit diffraction pattern of the zone of interest being associated with a microorganism known as a microorganism of interest;
  reading calibration data relating a value of a numerical indicator and a concentration of lipids in a microorganism of interest, for determining a concentration of lipids in the at least one microorganism of interest.

The dispersion of the light intensity herein refers to a statistical dispersion. This is the measurement according to which the values of the light intensity are dispersed. The dispersion can be measured by a standard deviation, an interquartile range, a variance, a range, a mean absolute deviation or another reference value, an r-order diameter and in particular a zero order diameter, or any other known measurement of a dispersion.

A zone of interest can be defined such that it comprises a single unit diffraction pattern.

Alternatively, a zone of interest can be defined such that it comprises a plurality of unit diffraction patterns, and a mean concentration of lipids in the microorganisms of interest is determined.

Preferably, the numerical indicator consists of a standard deviation of the light intensity relative to a reference light intensity.

Alternatively, the numerical indicator consists, for each unit diffraction pattern, of a difference between the light intensity in the center of said unit diffraction pattern and the light intensity of the first dark ring thereof.

The method according to the invention is advantageously implemented for performing an in situ follow-up of a culture of microorganisms in a pool or a bioreactor.

The invention also relates to a device for determining a concentration of lipids in a microorganism, in particular a micro-alga, comprising:
  a light source, arranged to illuminate a sample comprising microorganisms; and
  a matrix photodetector disposed facing the light source, arranged to acquire a total diffraction pattern of the sample, the total diffraction pattern comprising several unit diffraction patterns each associated with a microorganism.

The device according to the invention further comprises calculating means receiving as an input the total diffraction pattern, said calculating means comprising:
  means for determining a value of a numerical indicator representative of a dispersion of the light intensity in a zone of interest of the total diffraction pattern, said zone of interest comprising at least one unit diffraction pattern, and each unit diffraction pattern of the zone of interest being associated with a microorganism known as a microorganism of interest;
  means for reading calibration data relating a value of a numerical indicator and a concentration of lipids in a microorganism of interest, for outputting a concentration of lipids in the at least one microorganism of interest.

The device according to the invention can comprise:
  a first sealed housing, receiving the light source and having a first transparent window between the light source and the matrix photodetector;

a second sealed housing, receiving the matrix photodetector, and having a second transparent window between the first transparent window and the matrix photodetector;

the first sealed housing, the light source, the second sealed housing and the matrix photodetector forming together an immersible probe.

BRIEF DESCRIPTION OF THE DRAWINGS

The present invention will be better understood upon reading the description of exemplary embodiments given by way of purely indicating and in no way limiting purposes, making reference to the appended drawings in which.

DETAILED DISCLOSURE OF PARTICULAR EMBODIMENTS

A method according to the invention will first be described in reference to FIG. 1.

Step 101:

A sample containing microorganisms, in particular a sample containing micro-algae is illuminated.

The sample is for example an algal solution cultivated for several days in a medium known as an ESAW nitrogen rich medium. The ESAW medium corresponds to an artificial sea water, and is described by Harrison et al. in the review "*Journal of Phycology*" vol. 16, pages 28-35, 1980 and, in an improved version, by Berges et al. in the review "*Journal of Phycology*" vol. 37, pages 1138-1145, 2001. Nitrogen is essential for the algal growth. Micro-algae are further lighted at 40 photons/micro-Einstein, 12 hours per day and 12 hours per night, and subjected to a continuous stirring. The algae of the algal solution are precisely of the type *Phaeodactylum tricornutum* (Pt1) Bohlin Strain 8.6 CCMP2561 (available in the Phytoplankton Marine collection, nowadays called NCMA for "National Center for Marine Algae and Microbiota"). The concentration of micro-algae in the liquid sample is $1.10^6$ to $2.10^6$ micro-algae/mL.

The illumination corresponds to an illumination by the light source of lens-free imaging means which will be further described in the continuation.

Step 102:

Upon illuminating 101 the sample, a total diffraction pattern is acquired, that is a two dimension image comprising a plurality of diffraction patterns each associated with a micro-algae. In the continuation, a "unit diffraction pattern" refers to a diffraction pattern associated with a single micro-alga.

By way of illustration, an example of a total diffraction pattern 12 is represented on the right. The total diffraction pattern 12 corresponds to a diffraction pattern obtained using lens-free imaging means as will be described in the continuation and in reference to FIG. 5.

Step 103:

During a step 103, on the total diffraction pattern 12, a zone of interest 13 represented on the right in the figure is defined. The zone of interest 13 comprises at least one unit diffraction pattern 131. In the example represented in FIG. 1, the zone of interest 13 has a plurality of unit diffraction patterns. By "micro-alga of interest", it is meant a micro-alga associated with a unit diffraction pattern present in the zone of interest 13, in particular fully present in the zone of interest, or at least the center zone and the first dark ring of which are present in the zone of interest.

As explained in the continuation, generally, a unit diffraction pattern comprises a center zone the grey level of which is substantially homogeneous. This center zone is surrounded by concentric rings, centered on the center zone. The center zone can take the shape of a disc, in which case the rings are circular. It can also take another shape, for example an ellipse surface. When the center zone takes an ellipse surface shape, the rings have an ellipse shape.

The selection of a zone of interest 13 preferably responds to preset criteria. For example, a rectangle having a predefined height and width, and centered on a predetermined pixel of the image corresponding to the total diffraction pattern is selected. The zone of interest is thus an image with a size higher than or equal to that of the total diffraction pattern 12.

It can even be contemplated that the zone of interest 13 has the same dimensions as the total diffraction pattern 12. In this case, step 103 can be dispensed with.

Step 104:

Then, a value of a numerical indicator In, representative of a dispersion of the light intensity in the zone of interest 13 is determined.

The numerical indicator is for example a standard deviation of the light intensity in the zone of interest 13, relative to a reference intensity which can be the mean light intensity of this zone of interest 13. It can be a relative standard deviation, that is a ratio of the standard deviation to said reference intensity.

Alternatively, the numerical indicator is the difference between the light intensity in the center zone of a unit diffraction pattern 131 and the light intensity in the first dark ring of this unit diffraction pattern 131.

This alternative is particularly advantageous in the case where the zone of interest comprises a single unit diffraction pattern. In particular:

when the zone of interest comprises a single unit diffraction pattern 131, the numerical indicator can be the difference between the light intensity in the center zone and the light intensity in the first dark ring of this unit diffraction pattern 131;

when the zone of interest comprises several unit diffraction patterns, the numerical indicator can be a list of differences between the light intensity in the center zone and the light intensity in the first dark ring of each unit diffraction pattern, or a mean value of these differences.

Mean values of light intensity in said center zone and in said first dark ring can be taken into consideration. In other words, the difference between the light intensity in the center zone and the light intensity in the first dark ring of a unit diffraction pattern then corresponds to the difference between the mean light intensity in the center zone and the mean light intensity in the first dark ring of this unit diffraction pattern. Alternatively, this difference corresponds to the difference between the maximum light intensity in the center zone and the minimum light intensity in the first dark ring of this unit diffraction pattern.

In the case where the zone of interest comprises several unit diffraction patterns, the unit diffraction patterns can be considered separately. The numerical indicator is then a list of differences between the light intensity in the center zone and the light intensity in the first dark ring, for each unit diffraction pattern of the zone of interest. Preferably, the numerical indicator is however a mean value of these differences.

Step 105:

Then, the calibration data relating a value of the numerical indicator and a concentration of lipids in micro-algae is read, to relate the calculated value of the numerical indicator to the concentration of lipids in the micro-algae of the previously selected zone of interest. As the value taken by the numerical indicator is known, a concentration of lipids $C_x$ in the micro-algae of interest is deduced therefrom, thanks to the calibration data.

The calibration data can consist of a curve relating a value of the numerical indicator In and a concentration C of lipids in the micro-algae.

Alternatively, there is not one curve but only one or several points relating a value of the numerical indicator In and a concentration C. In this case, the concentration of lipids in the micro-algae of interest is a concentration range.

The calibration data are typically determined during a prior calibration step, during which the numerical indicator corresponding to micro-algae having a known concentration of lipids is measured. During this calibration step, for example several points relating a value of the numerical indicator and a concentration of lipids is acquired, and then a curve is deduced therefrom by interpolating these points.

This calibration step has to be implemented under predetermined set experimental conditions, such that between two measurements, the contrast is not modified otherwise than by the algal solution itself. These experimental conditions are in particular the nature, position and emission power of a light source used for illuminating the sample, and the nature and the position of a sensor used to acquire the total diffraction pattern.

The calibration step can enable usable calibration data to be gathered regardless of the dimensions of the zone of interest then used for implementing the method according to the invention. It can be seen for example that the standard deviation of a distribution of light intensities in an image does not depend on the size of this image.

It can be advantageous to take the concentration of micro-algae in the algal solution into account. In this case, a two dimension calibration is performed by varying both the concentration of lipids of the micro-algae and their concentration in the algal solution. In practice, an algal solution with a known concentration will be advantageously available, which will enable a concentration of lipids to be determined as a function of a value of the numerical indicator and this concentration.

As a function of the concentration of micro-algae in the algal solution, minimum dimensions can also be determined for the zone of interest, making it possible to make sure to average a sufficient number of unit diffraction patterns to obtain representative results.

Step 106:

Step 106 corresponds to providing the concentration of lipids $C_x$ in the micro-algae of interest.

It is for example the mean concentration of lipids in the micro-algae of interest, or a concentration range of lipids in the micro-algae of interest.

Figure 1:
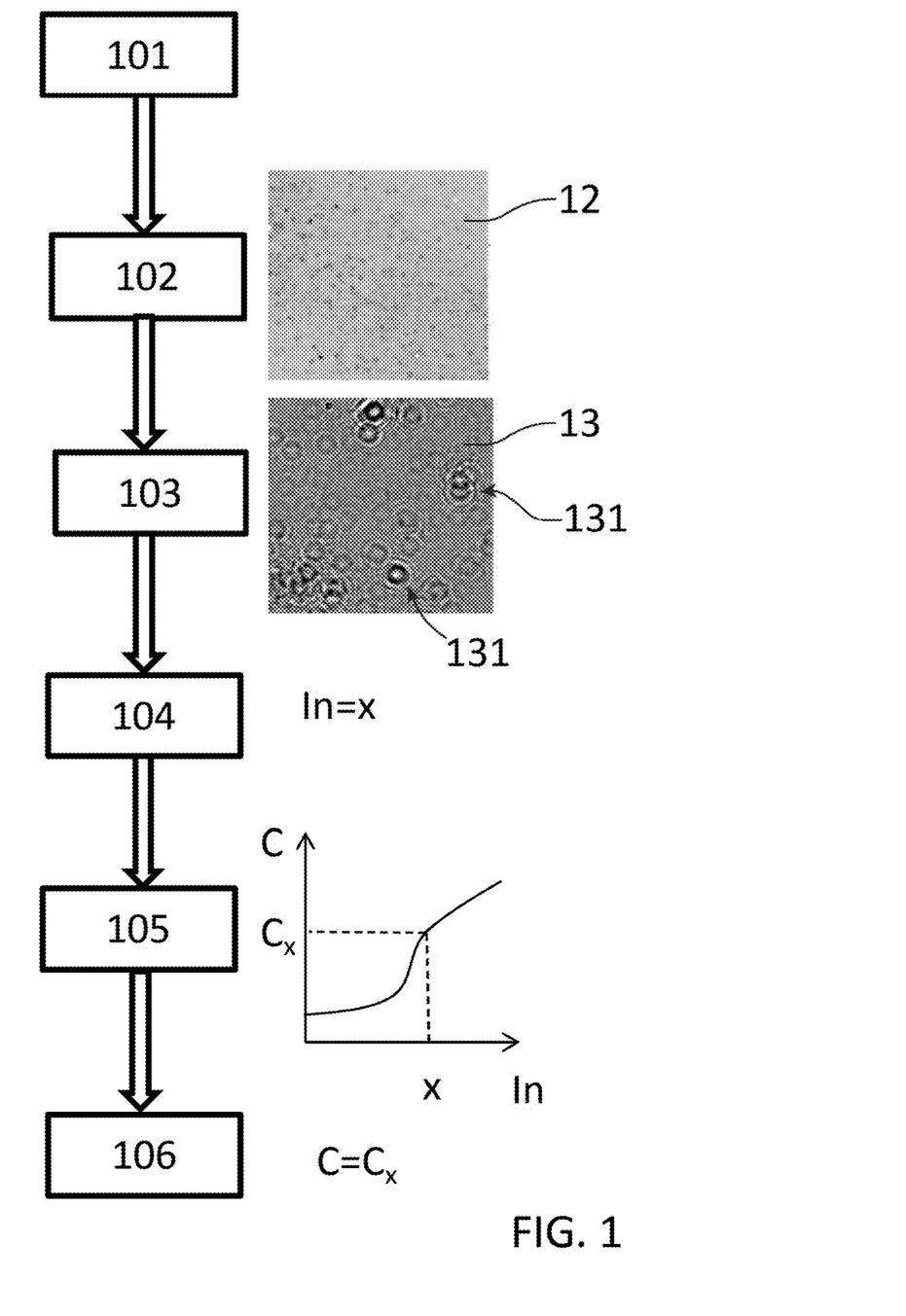
FIG. 1 schematically illustrates a method according to the invention.
Figure 2A:
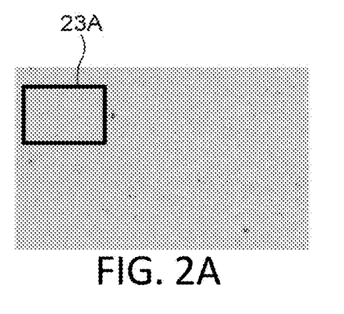
FIGS. 2A and 2B illustrate total diffraction patterns according to the invention, respectively in the case of lipid-rich and lipid-poor microorganisms.

FIG. 2A illustrates a total diffraction pattern of a sample as defined in reference to FIG. 1, and having a strong lipid content. This strong lipid content herein corresponds to a triacylglycerol content having a value between 20 and 80% dry weight. The dry weight corresponds to the mass of the micro-algae after they have been isolated from the solution (for example by centrifugation), and then lyophilized. The corresponding sample has been obtained from the above-described algal solution, and then incubated for three days in a nitrate (herein $NO_3^-$)-poor medium, therefore a nitrogen-poor medium. In the absence of nitrogen, the micro-algae tend to grow and produce lipids. In the present case, the molar concentration of $NO_3^-$ is 0 mol/L.

In FIG. 2A, a zone of interest 23A as defined in reference to FIG. 1, and comprising several unit diffraction patterns, is illustrated.

Figure 2B:
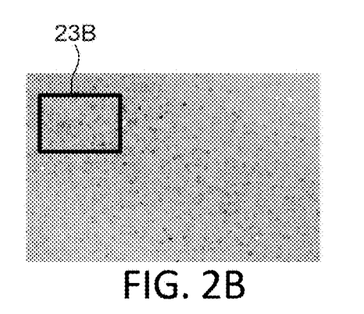

FIG. 2B illustrates a total diffraction pattern of a sample as defined in reference to FIG. 1, and having a low lipid content. This low lipid content here corresponds to a triacylglycerol content having a value between 0 and 10% of dry weight. The corresponding sample has been obtained from the above-described algal solution, and then incubated for three days in a nitrate (herein $NO_3^-$)-rich, thus nitrogen-rich medium. In the presence of nitrogen, the micro-algae produce little or no lipid. In the present case, the molar concentration of $NO_3^-$), is 0.55 mmol/L.

In FIG. 2B, is illustrated a zone of interest 23B as defined in reference to FIG. 1, and comprising several unit diffraction patterns.

FIGS. 2A and 2B are obtained using a CMOS sensor having an area of 24 mm$^2$, having a pixel pitch of 2.2 µm. On the sensor, a microscope slide with an area of 25×70 mm$^2$ is placed, on which a drop of the algal solution has been deposited.

Figure 3A:
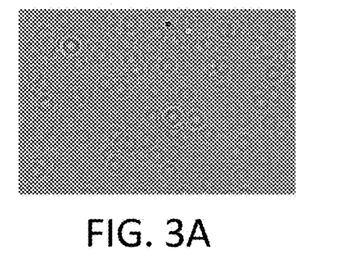
FIGS. 3A and 3B illustrate zones of interest according to the invention, respectively in the case of lipid-rich and lipid-poor microorganisms.
Figure 3B:
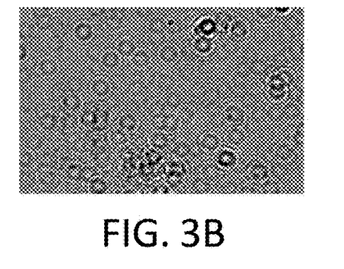

FIG. 3A illustrates the zone of interest 23A represented in FIG. 2A. FIG. 3B illustrates the zone of interest 23B represented in FIG. 2B. In these figures, the width of a diffraction pattern is about 100 µm (diameter of the first dark ring).

It can be seen in FIGS. 3A and 3B that a zone of interest corresponding to lipid-rich micro-algae can be optically recognized because the unit diffraction patterns have a low contrast. In the same way, a zone of interest corresponding to lipid-poor micro-algae can be optically recognized because the unit diffraction patterns have a high contrast.

For each zone of interest, the standard deviation of the light intensity has been measured relative to the mean light intensity.

In the case of FIG. 3A, the signal has an average grey level of 216, a standard deviation of 14.0, that is a relative standard deviation of 6.48%. The grey level will be defined in reference to FIG. 4C.

In the case of FIG. 3B, the signal has a mean grey level of 195, a standard deviation of 31.7, that is a relative standard deviation of 16.3%.

The ratio between both relative standard deviations is sufficiently high (ratio 2.5) to be a discriminant criterion of the concentration of lipids in a micro-alga.

It is deduced therefrom that:
when this relative standard deviation is higher than 16.5%, the concentration of lipids in a micro-alga is substantially lower than 10% of dry weight;

when this relative standard deviation is between 6.5 and 16.5%, the concentration of lipids in a micro-alga is substantially between 10% and 20% of dry weight; and when this relative standard deviation is lower than 6.5%, the concentration of lipids in a micro-alga is substantially higher than 20% of dry weight.

Figures 4A, 4B, 4C:
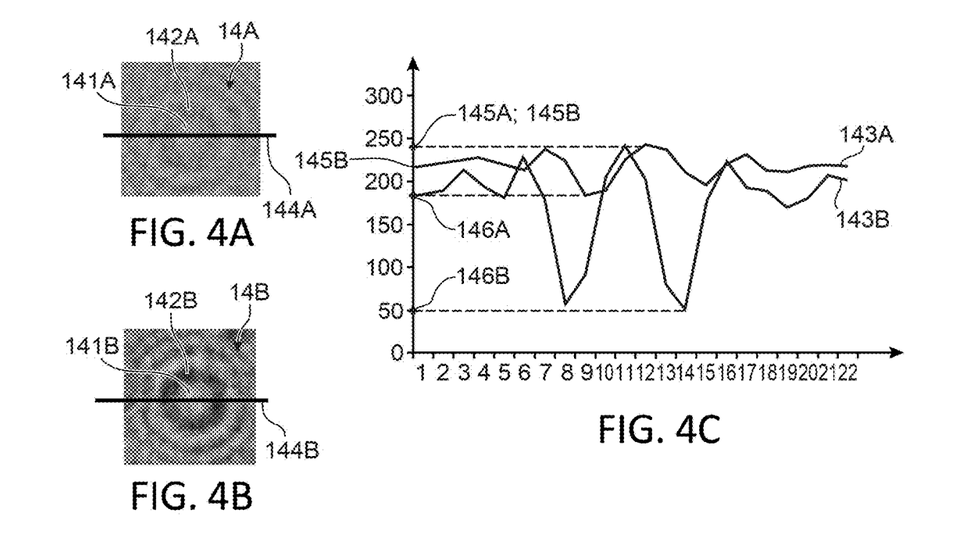
FIGS. 4A and 4B illustrate unit diffraction patterns according to the invention, respectively in the case of lipid-rich and lipid-poor microorganisms.
FIG. 4C illustrates cross-sections of the unit diffraction patterns represented in FIGS. 4A and 4B.

FIG. 4A illustrates a unit diffraction pattern 14A associated with a lipid-rich micro-alga. It is a detail view of FIG. 3A. It can be seen that the difference in light intensity between the center zone 141A and the first dark ring 142A is low.

FIG. 4B illustrates a unit diffraction pattern 14B associated with a lipid-poor micro-alga. It is a detail view of FIG. 3B. It can be seen that the difference in light intensity between the center zone 141B and the first dark ring 142B is high.

Therefore, a concentration of lipids in a micro-alga can be determined from its unit diffraction pattern, for example by determining the mean light intensity in the center zone, the mean light intensity in the first dark ring, and then the difference between both.

It can be considered that FIGS. 4A and 4B each correspond to a zone of interest having a single unit diffraction pattern.

Here, each micro-alga produces a unit diffraction pattern comprising a bright center disk (corresponding to a strong light intensity), surrounded by alternate dark and bright rings. A modification in the geometry of a micro-alga (for example the geometry of its outer shell and/or its core), will result in a modification of the unit diffraction pattern associated therewith. For example, an oval center surface, surrounded by closed bright and dark oval shaped curves will be obtained. The unit diffraction pattern associated with a micro-alga will always have a succession of closed concentric curves, which will also be referred to "diffraction rings" by misuse of language. These closed curves surround a surface called a center zone.

The diffraction laws enable the dimensions of the center zone and those of the first dark ring to be predicted. There is in particular for a micro-alga having a circular profile geometry, a unit diffraction pattern which corresponds to an Airy disk. In particular, the diameter of the smallest dark ring is defined by the distance between the micro-alga and the photodetector, and by an angle θ such that sin $$\theta = 1.22 \frac{\lambda}{d},$$

where λ is the emission wavelength of the light source, and d is the diameter of the circular profile. Therefore, for example the dimensions of a zone of interest can be deduced therefrom such that it comprises a single unit diffraction pattern. By using also an even very coarse shape recognition method, the zone of interest can then be centered on the center of a unit diffraction pattern.

Since each unit diffraction pattern herein has an axial symmetry, a cross-section of a unit diffraction pattern passing through the axis of symmetry can be studied. FIG. 4C corresponds to cross-sections of two diffraction patterns.

In FIG. 4C, the ordinate axis is graduated in grey levels (from 0 to 255, that is 256 grey levels for an analog signal output from a photodetector converted into a digital signal coded on 8 bits). A low value of grey level corresponds to a low light intensity. A strong value of grey level corresponds to a strong light intensity. The abscissa axis is graduated in pixels.

Curve 143A corresponds to a cross-section of the unit diffraction pattern represented in FIG. 4A and passes through the axis 144A intersecting the center of symmetry of the unit diffraction pattern.

Curve 143B corresponds to a cross-section of the unit diffraction pattern represented in FIG. 4B and passing through the axis 144B intersecting the center of symmetry of the unit diffraction pattern.

In FIG. 4C, the axis of symmetry of each unit diffraction pattern is recognized. Curves 143A and 143B are positioned on the figure such that their axes of symmetry are substantially aligned with each other.

In FIG. 4C, one can distinguish:
the intensity maximum 145A of curve 143A, located in the center zone 141A;
the intensity maximum 145B of curve 143B, located in the center zone 141B (herein the same as the intensity maximum 145A);
the intensity minimum 146A of curve 143A, located in the first dark ring 142A; and
the intensity minimum 146B of curve 143B, located in the first dark ring 142B.

The deviation between the maximum 145A and the minimum 146A is then 50, whereas the deviation between the maximum 145B and the minimum 146B is about 200. The ratio between both deviations is high enough (ratio 4) to be a discriminant criterion of the concentration of lipids in a micro-alga.

It is deduced therefrom that:
when this deviation is higher than 200, the concentration of lipids in a micro-alga is substantially lower than 10% of dry weight;
when this deviation is between 50 and 200, the concentration of lipids in a micro-alga is substantially between 10% and 20% of dry weight; and
when this deviation is lower than 50, the concentration of lipids in a micro-alga is substantially higher than 20% of dry weight.

Therefore, it can be seen that the invention provides an advantageous method enabling a concentration of lipids in micro-algae to be determined.

This method requires a simple illumination of a sample, and an acquisition of a diffraction pattern. Therefore, it is not destructive.

Besides, this method enables a plurality of unit diffraction figures making up a diffraction figure to be simultaneously analyzed, each unit diffraction pattern being associated with a microorganism. This enables the lipid content of a great number of microorganisms to be characterized at the same time and statistical indicators such as the mean or variance to be available. On the other hand, by reproducing the method overtime, information about the time evolution of the lipid content is obtained.

Further, since it is here not attempted to rebuild the image of a micro-alga, it is not necessary to know the distance between the micro-alga and a sensor for acquiring the total diffraction pattern. A population of micro-algae contained in a volume, and not only in a plane can thus be easily analyzed. It is no longer necessary to provide focusing on a particular plane either, which enables once again a population of micro-algae contained in a volume to be easily analyzed.

Further, as illustrated in the continuation, the hardware means for implementing this method are simple and inexpensive: these are in particular lens-free imaging means. The imaging means do not require the use of expansive optics. The invention does not require the use of very powerful computational means either, because it is not attempted to rebuild an image of the micro-algae from their unit diffraction patterns. It is not attempted to process the unit diffraction patterns either to compare them to a library of reference diffraction patterns to them implement heavy shape recognition methods.

Since the calculations implemented are simple, the time for processing information can be very short, lower than one second. Within the scope of an in situ follow-up of a culture, this enables an abnormality (due for example to an interference) to be quickly found and the suitable correction (for example by decontaminating the culture) to be conducted soon enough.

Another advantage of the method according to the invention is its accuracy: accurate measurements can be made on each micro-alga considered individual, from its unit diffraction pattern.

A first embodiment of a device 500 according to the invention will now be described in reference to FIG. 5. The device 500 according to the invention is preferably adapted to implement the method according to the invention.

The device 500 comprises in particular lens-free imaging means comprising a light source 551 and a sensor 552. The lens-free imaging means are known to those skilled in the art, which will readily be able to find details for making such a device in literature.

A light source 551 emits a light beam 553 illuminating the sample 554. A light source is preferably spatially coherent. The light source can be a laser diode, or a Light Emitting Diode (LED) followed by a filtering hole. The filtering hole enables the spatial coherence of the light beam emitted by the LED to be improved. Advantageously, the light source is also temporally coherent.

A LED the initial spectrum of which is centered on 490 nm, that is a blue emission, is for example used. The width of the peak at 490 nm is 40 nm. The emission power of the LED is for example between 100 mW and 1 W. The LED is followed by a filtering hole with a diameter 150 µm, directly placed in contact with the LED.

The sample 554 is placed between the light source 551 and the sensor 552 here consisting of a matrix photodetector.

Figure 5:
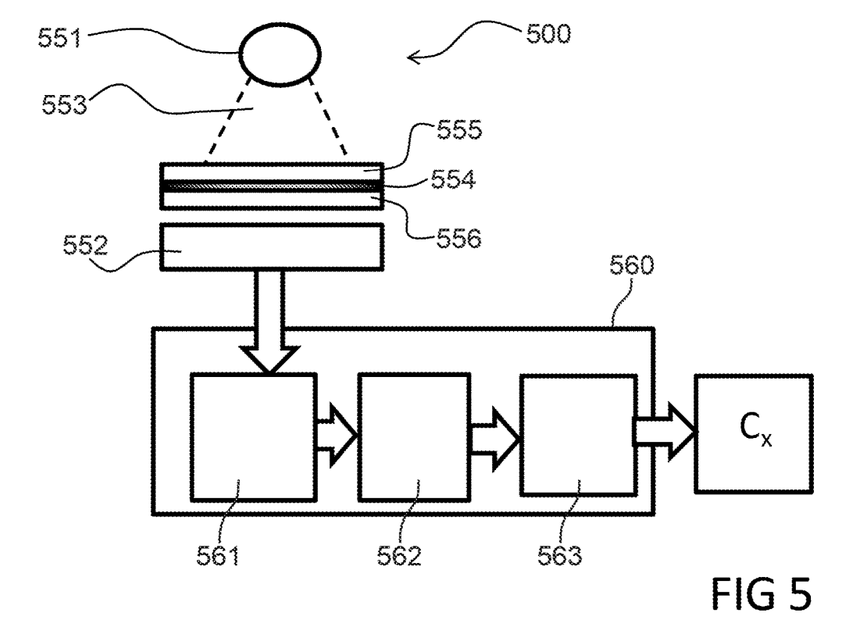
FIG. 5 schematically illustrates a first embodiment of a device according to the invention.

In the example represented in FIG. 5, the sample is placed between two slides 555,556 transparent to the emission wavelength of the light source. The device 500 according to the invention thus works in transmission. The distance between the slide 555 (on the light source side) and the light source is generally between 1 cm and 10 cm.

The sample is for example a sample of a micro-algal solution as described in reference to FIG. 1. The device 500 enables micro-algae contained in the sample and having a low diameter, typically between 100 nm and 500 µm, typically between 50 µm and 200 µm to be investigated.

The matrix photodetector 552 converts an incident electromagnetic radiation into an analog electric signal. This matrix photodetector 552 is also connected to an analog-digital converter so as to provide a digital image. This is known as a matrix photodetector, because the detection surface of the photodetector is cut-off into pixels forming a matrix. The matrix photodetector 552 is for example a CCD sensor (Charge-Coupled Device) sensor or a CMOS (Complementary Metal Oxide Semiconductor) sensor. Each pixel of the photodetector is for example a square with a side lower than 9 µm, and even lower than 5 µm, for example 2.2 µm. In particular, a CMOS sensor of 42.9×57.6 mm$^2$, having a pixel pitch of 2.2 µm can be used.

The matrix photodetector 552 detects a diffraction pattern corresponding to the influence of the micro-algae of the sample 554 on the light beam 553. In particular, the matrix photodetector 552 detects a diffraction pattern corresponding to the interferences between incident light waves directly coming from the light source 551 and light waves emitted by the light source and then diffracted by micro-algae of the sample 554. This diffraction pattern corresponds to the previously described total diffraction pattern. Each unit diffraction pattern therefore corresponds to the interferences between waves directly coming from the light source 551 and waves emitted by the light source and then diffracted by a micro-alga in particular.

Such a diffraction pattern is often referred to as a "hologram". One advantage of such a diffraction pattern is that the signal detected has a large amplitude, thanks to the contribution of the signal directly coming from the light source. Another advantage of this diffraction pattern is that the field of view detected is wide because it is determined by the sensor size, for example higher than 20 mm$^2$. Unit diffraction patterns corresponding to many micro-algae, for example up to ten thousand can be simultaneously imaged.

Le photodetector 552 is positioned in the proximity of the sample 554, for example at 0.8 mm from the slide 556 (slide on the photodetector 552 side).

Therefore, using the device 500 according to the invention, a diffraction pattern corresponding to an object, and not directly the image of this object is detected. This technique is referred to as "lens-free imaging". It should be noted that lens-free imaging means can comprise an array of microlenses, used for focusing on each pixel the beam corresponding to interferences to be detected. However, they do not include magnification optics disposed between the object and the photodetector.

Those skilled in the art will be readily able to position each of the elements among the light source 551, the sample 554 and the photodetector 552 with respect to each other.

A support (not represented) can be provided to receive the sample 554, this support being disposed between the light source 551 and the photodetector 552.

In the example represented, the sample 554 is a volume sample: the thickness between both slides 555, 556 is for example 0.2 mm. The volume of the sample 554, imaged on the photodetector 552 in the form of a diffraction pattern, is about 5 µL.

The device 500 according to the invention comprises calculating means 560 receiving as an input the total diffraction pattern acquired by the photodetector 552.

The total diffraction pattern 500 is received by means 561 for selecting in the total diffraction pattern a zone of interest such as described in reference to FIG. 1 and about step 103. The means 561 advantageously comprise electronic means and computing and/or software means, implementing an algorithm selecting part of an image as a function of predefined criteria contained in a memory such as the dimensions of the part of image to be selected. The means 561 can be dispensed with in the case where the zone of interest corresponds to the entire total diffraction pattern.

The image corresponding to this zone of interest is transmitted to means 562 for determining a value of a numerical indicator representative of a dispersion of the light intensity in the zone of interest (see step 104 of the method illustrated in reference to FIG. 1). The means 562 advantageously comprise electronic means and computing and/or software means, implementing an algorithm for measuring grey levels in an image to calculate such a numerical indicator.

The calculated value of the numerical indicator is transmitted to means 563 for reading calibration data relating a value of a numerical indicator and a concentration of lipids in a microorganism of interest, to determine a concentration of lipids in the at least one microorganism of interest (see step 105 of the method illustrated in reference to FIG. 1). The means 563 advantageously comprise electronic means and computing and/or software means, implementing:

- an algorithm for comparing numerical data (to locate the calculated value of the numerical indicator on the abscissa axis of a calibration curve, or in an interval among several intervals each corresponding to an interval between the abscissae of two calibration points); and
- an algorithm for reading tables or reading curves (to determine the concentration of lipids associated with a position on the abscissa axis of the calibration curve or an interval between two concentrations which is associated with an interval between the abscissae of two calibration points).

The concentration of lipids $C_x$ thus obtained is outputted by the calculating means 560.

It can be seen that the device according to the invention is particularly simple, since the imaging means are minimum and the calculating means do not require a high computational power, since the processings made by the latter are simple.

Figure 6:
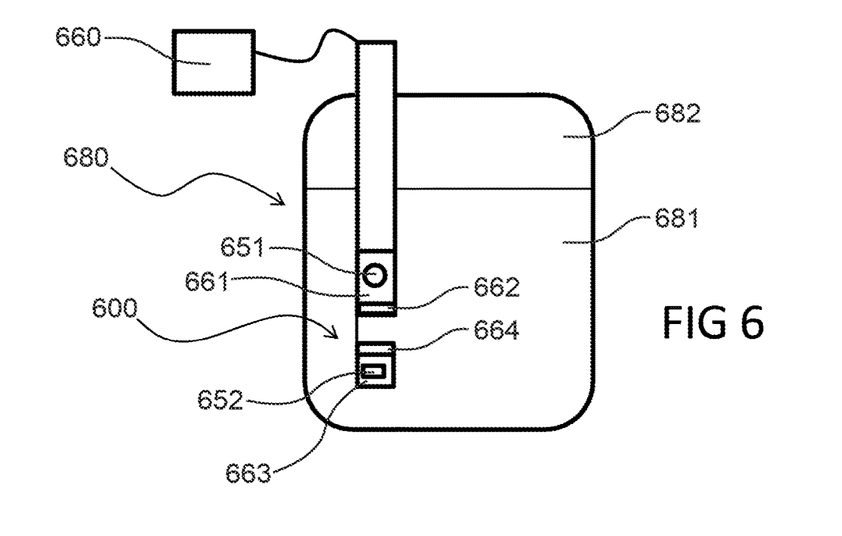
FIG. 6 schematically illustrates a use of a second embodiment of the device according to the invention.

FIG. 6 illustrates a use of a second embodiment of the device according to the invention. In FIG. 6, reference numerals 600, 651, 652, 660 respectively correspond to reference numerals 500, 551, 552, 560 of FIG. 5.

The device 600 according to the invention comprises:

- a first sealed housing 661 receiving the light source 651, and closed by a first transparent window 662; and
- a second sealed housing 663 receiving the photodetector 652, and closed by a second transparent window 664.

The first sealed housing 661 receiving the light source 651, and the second sealed housing 663 receiving the photodetector 652, form together a probe immersible in a liquid solution. The sample is thereby formed by a liquid solution portion located between the first and the second transparent windows. The transparent windows typically delimit a volume of 5 μL, and are spaced a part by about 200 μm from each other. Alternatively, the distance between the transparent windows can be variable, such that this distance can be adjusted to have the same number of micro-algae between the transparent windows regardless of the concentration of micro-algae in the liquid solution.

The immersible probe is connected to the calculating means 660 wirelessly or by wire.

The device 600 is placed in a bioreactor 680, in particular a photobioreactor, that is a closed container enabling the micro-alga culture conditions (temperature, pH, nutriments, $CO_2$) to be perfectly controlled. A photobioreactor has a large area/volume ratio, which restricts the lighting heterogeneity on micro-algae. This closed container enables contamination of the micro-algae by parasites, and conversely, the contamination of the external environment by the micro-algae to be avoided.

The bioreactor 680 receives, in a vessel 682, a liquid solution 681 comprising micro-algae. Apertures provided in the vessel 682 enable probes to be inserted in order to control the conditions inside a bioreactor 680. One of these apertures is used to insert the immersible probe as defined above. The immersible probe has an upper part receiving the first sealed housing as described hereinbefore, and a lower part receiving the second sealed housing as described herein before. The space between both these housings is occupied by the liquid solution.

The immersible probe has an elongated cylinder shape, with a diameter lower than 12 mm and a length higher than 50 mm. Its dimensions do not require the existing bioreactors to be modified.

The cylinder receives for example an electronic board managing the acquisition of images by the photodetector and the light source power supply, this board being remotely driven by a processor receiving the calculating means.

The device 600 according to the invention enables the time evolution of a concentration of lipids in the micro-algae of the liquid solution to be measured, for example to determine the time when the concentration of lipids is sufficient to conduct lipid extraction. In situ follow-up does not require the presence of a human operator, since the method according to the invention can be automated.

The time for acquiring a total diffraction pattern is advantageously in the order of one millisecond, to avoid the movement effect of the micro-algae.

Alternatively, an in situ follow-up can be made in an open air pool used for cultivating micro-algae.

Throughout the text, micro-algae are considered, but other types of microorganisms, such as for example cyanobacteria could also be contemplated.

Besides the field of biofuels, the study of the concentration of lipids in micro-algae has numerous applications:

- in the food-processing field, for manufacturing dietary supplements, or manufacturing animal (livestock, fish) feed;
- in the field of biotechnologies, for producing high added value molecules, or for screening to explore biodiversity or isolate promising mutants from a micro-algae bank.

The invention claimed is:

1. A method for determining a concentration of lipids in at least one microorganism of interest, comprising the following steps:

illuminating a sample containing microorganisms;

acquiring a total diffraction pattern of the sample, the total diffraction pattern comprising a plurality of unit diffraction patterns each associated with a microorganism, wherein each unit diffraction pattern comprises a center zone surrounded by concentric rings centered on the center zone;

determining a value of a numerical indicator (In) representative of a dispersion of the light intensity in a zone of interest of the total diffraction pattern, said zone of interest comprising at least one unit diffraction pattern, and each unit diffraction pattern of the zone of interest being associated with a microorganism known as the at least one microorganism of interest; and reading calibration data relating a value of a numerical indicator (In) and a concentration (C) of lipids in the at least one microorganism of interest, for determining a concentration of lipids ($C_x$) in the at least one microorganism of interest.

2. The method according to claim 1, wherein the zone of interest is defined to comprise a single unit diffraction pattern.

3. The method according to claim 1, wherein the zone of interest is defined to comprise a plurality of unit diffraction patterns, and in that a mean concentration of lipids in the at least one microorganism of interest is determined.

4. The method according to claim 1, wherein the numerical indicator (In) is a standard deviation of the light intensity in a zone of interest of the total diffraction pattern relative to a reference light intensity.

5. The method according to claim 1, wherein the numerical indicator (In) is, for each unit diffraction pattern, a difference between the light intensity in the center of said unit diffraction pattern and the light intensity of a first dark ring thereof.

6. The method according to claim 1, which is conducted in an in situ follow up of a culture of microorganisms in a pool or a bioreactor.

7. The method according to claim 1, wherein the at least one microorganism of interest is at least one micro-alga.

8. A device configured to determine a concentration of lipids in at least one microorganism of interest, comprising:
   a light source, arranged to illuminate a sample comprising microorganisms; and
   a matrix photodetector disposed facing the light source, arranged to acquire a total diffraction pattern (12) of the sample, the total diffraction pattern comprising several unit diffraction patterns each associated with a microorganism; characterized by calculating means receiving as an input the total diffraction pattern, said calculating means comprising:
   means for determining a value of a numerical indicator (In) representative of a dispersion of the light intensity in a zone of interest of the total diffraction pattern, said zone of interest comprising at least one unit diffraction pattern, and each unit diffraction pattern of the zone of interest being associated with a microorganism known as the at least one microorganism of interest, wherein each unit diffraction pattern comprises a center zone surrounded by concentric rims centered on the center zone;
   means for reading calibration data relating a value of a numerical indicator (In) and a concentration (C) of lipids in the at least one microorganism of interest, for outputting a concentration of lipids ($C_x$) in the at least one microorganism of interest.

9. The device according to claim 8, further comprising:
   a first sealed housing, receiving the light source and having a first transparent window between the light source and the matrix photodetector;
   a second sealed housing, receiving the matrix photodetector, and having a second transparent window between the first transparent window and the matrix photodetector;
   the first sealed housing, the light source, the second sealed housing and the matrix photodetector forming together an immersible probe.

10. The device according to claim 8, wherein the at least one microorganism of interest is at least one micro-alga.

* * * * *